United States Patent
Imberty et al.

(10) Patent No.: US 10,247,734 B2
(45) Date of Patent: Apr. 2, 2019

(54) LECTINS AND APPLICATIONS FOR THE DETECTION OF PATHOLOGICAL STATE MARKERS

(71) Applicants: CENTRE NATIONAL DE LA RECHERCHE SCIENTIFIQUE CNRS, Paris (FR); UNIVERSITE JOSEPH FOURIER, Grenoble (FR)

(72) Inventors: Anne Imberty, Claix (FR); Aymeric Audfray, Biviers (FR); Julie Arnaud, Bellentre (FR)

(73) Assignees: CENTRE NATIONAL DE LA RECHERCHE SCIENTIFIQUE CNRS, Paris (FR); UNIVERSITE JOSEPH FOURIER, Grenoble (FR)

( * ) Notice: Subject to any disclaimer, the term of this patent is extended or adjusted under 35 U.S.C. 154(b) by 0 days.

(21) Appl. No.: 15/123,138

(22) PCT Filed: Feb. 26, 2015

(86) PCT No.: PCT/IB2015/051422
§ 371 (c)(1),
(2) Date: Sep. 1, 2016

(87) PCT Pub. No.: WO2015/132699
PCT Pub. Date: Sep. 11, 2015

(65) Prior Publication Data
US 2017/0074887 A1    Mar. 16, 2017

(30) Foreign Application Priority Data
Mar. 4, 2014    (FR) ..................... 14 51740

(51) Int. Cl.
C07K 14/42     (2006.01)
G01N 33/68     (2006.01)
C07K 14/47     (2006.01)

(52) U.S. Cl.
CPC ......... *G01N 33/68* (2013.01); *C07K 14/4726* (2013.01); *G01N 2333/4724* (2013.01); *G01N 2440/38* (2013.01); *G01N 2570/00* (2013.01)

(58) Field of Classification Search
CPC . G01N 2333/42; C07K 14/4726; C07K 14/42
See application file for complete search history.

(56) References Cited

PUBLICATIONS

Audfray et al. 2012. Fucose-binding lectin from opportunistic pathogen Burkholderia ambifaria binds to both pland and human oligosaccharidic epitopes. J. Bio. Chem. 287(6): 4335-4347.*
Arnaud et al. Nov. 2013; Reduction of lectin valency drastically changes glycodynamics in membranes but not surface avidity. Glycobiology. 23(11): 1382) as evidenced by Kostlanova et al. 2005; The fucose-binding lectin from Ralstonia solanacearum. J. Biol. Chem. 280(30): 27839-27849.*
Kostlanova et al. 2005; The fucose-binding lectin from Ralstonia solanacearum. J. Biol. Chem. 280(30): 27839-27849.*
Yadid et al. 2010; Metamorphic proteins mediate evolutionary transitions of structure. Proc. Natl. Acad. Sci. 107(16): 7287-7292.*
Romano et al. 2011; Development of recombinant Aleuria aurantia lectins with altered binding specificities to fucosylated glycans. Biochem. Biophys. Res. Comm. 414: 84-89.*
Cioci, G., et al: "β-Propeller Crystal Structure of Psathyrella velutina Lectin: An Integrin-like Fungal Protein Interacting with Monosaccharides and Calcium", Journal of Molecular Biology, Academic Press, United Kingdom, vol. 357, No. 5, Apr. 14, 2006 (Apr. 14, 2006), pp. 1575-1591, XP024950890, ISSN: 0022-2836, DOI: 10.1016/J.JMB.2006.01.066,[retrieved on Apr. 14, 2006].
Yadid, I., et al: "Functional β-propeller lectins by tandem duplications of repetitive units", Protein Engineering Design and Selection, vol. 24, No. 1-2, Aug. 16, 2010 (Aug. 16, 2010), pp. 185-195, XP055151982, ISSN: 1741-0126, DOI: 10.1093/protein/gzq053.
Yadid, I., et al: "Reconstruction of Functional β-Propeller Lectins via Homo-oligomeric Assembly of Shorter Fragments", Journal of Molecular Biology, Academic Press, United Kingdom, vol. 365, No. 1, Nov. 30, 2006 (Nov. 30, 2006), pp. 10-17, XP005728203, ISSN: 0022-2836, DOI: 10.1016/J.JMB.2006.09.055.
Yadid, I., et al: "Metamorphic proteins mediate evolutionary transitions of structure", Proceedings of the National Academy of Sciences, vol. 107, No. 16, Apr. 5, 2010 (Apr. 5, 2010), pp. 7287-7292, XP055152333, ISSN: 0027-8424, DOI: 10.1073/pnas.0912616107.
Cao, Z., et al: "Modulation of Glycan Detection on Specific Glycoproteins by Lectin Multimerization", Analytical Chemistry, vol. 85, No. 3, Feb. 5, 2013 (Feb. 5, 2013), pp. 1689-1698, XP055151987, ISSN: 0003-2700, DOI: 10.1021/ac302826a.
Wimmerova, M., et al: "Crystal Structure of Fungal Lectin: Six-Bladed β-Propeller Fold and Novel Fucose Recognition Mode for Aleuria Aurantia Lectin", Journal of Biological Chemistry, American Society for Biochemistry and Molecular Biology, US, vol. 278, No. 29, Jul. 18, 2003 (Jul. 18, 2003), pp. 27059-27067, XP008137663, ISSN: 0021-9258, DOI: 10.1074/JBC.M302642200, [retrieved on Mar. 5, 2003].
Vijayan, M., et al: "Lectins", Current Opinion in Structural Biology, Elsevier Ltd, GB, vol. 9, No. 6, Dec. 1, 1999 (Dec. 1, 1999), pp. 707-714, XP002177512, ISSN: 0959-440X, DOI: 10.1016/50959-440X(99)00034-2.

(Continued)

*Primary Examiner* — Karen Cochrane Carlson
(74) *Attorney, Agent, or Firm* — Young & Thompson

(57) ABSTRACT

Multimenic lectins having a β-propeller architecture, formed from monomer modules of approximately 30 to 60 amino acids, in which the binding sites to the glycans are situated on a given side of the proteins and the O-terminus and N-terminus ends of the peptide chains on the other side of the proteins, characterized in that they are formed from 4 to 7 monomer modules, a single, or a plurality of, or all of the adjacent modules being linked to one another by the linkers linking the N-terminus end of one module to the C-terminus end of the adjacent module.

Figure 1:
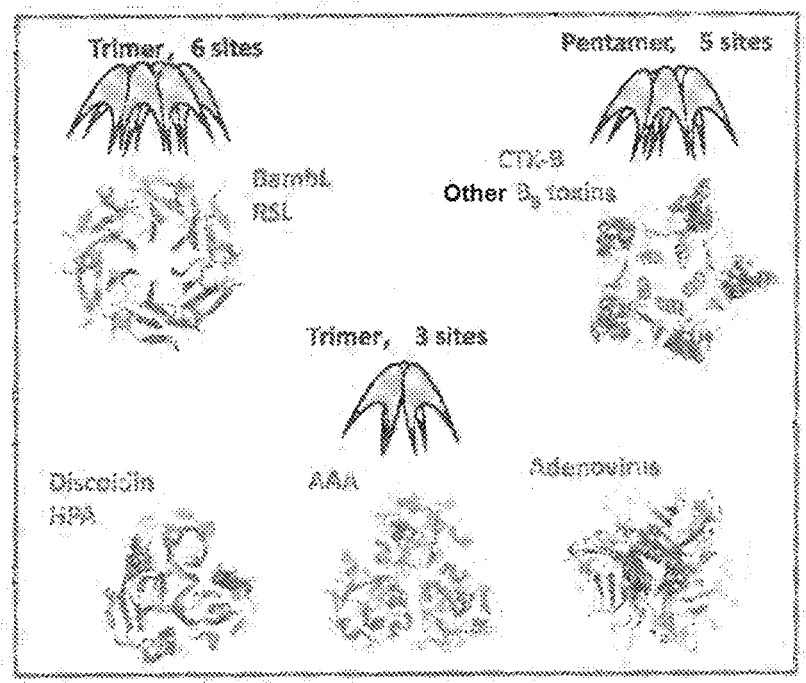

8 Claims, 4 Drawing Sheets
Specification includes a Sequence Listing.

(56) References Cited

PUBLICATIONS

International Search Report, dated May 7, 2015, from corresponding PCT Application.
Hu, D., et al., Directed Evolution of Lectins with Sugar-Binding Specificity for 6-Sulfo-Galactose, Journal of Biological Chemistry, vol. 287, No. 24, 2012, pp. 20313-20320.

* cited by examiner

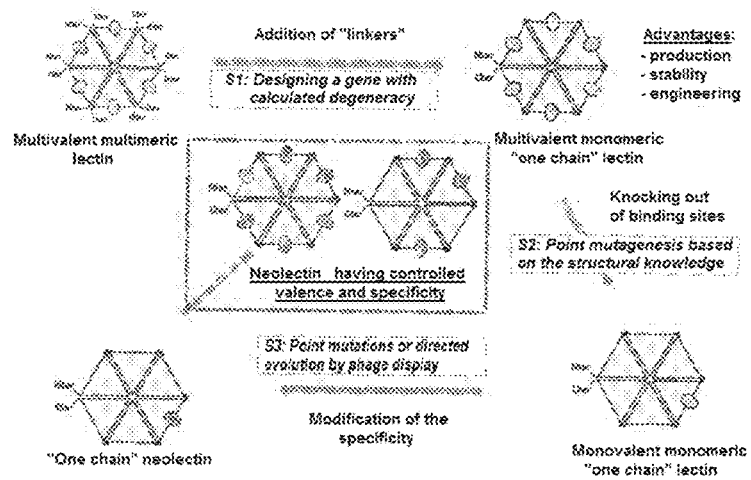
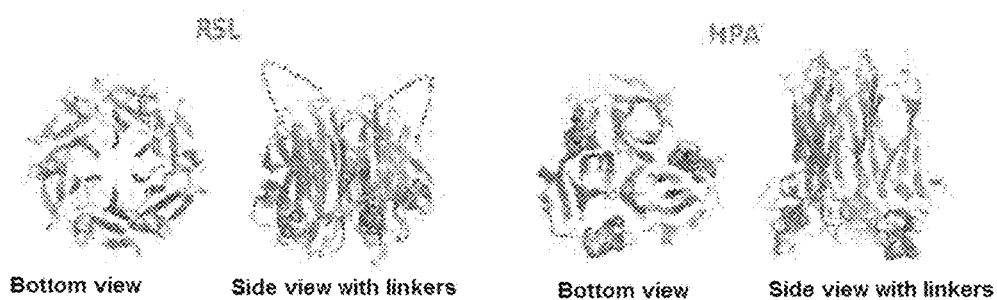

Figure 5
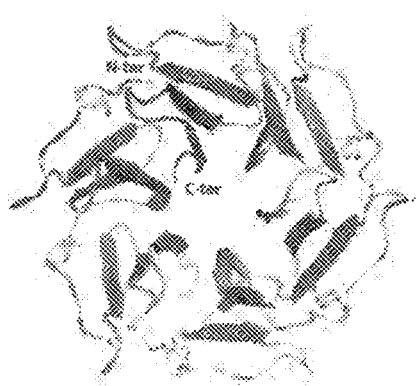
5A
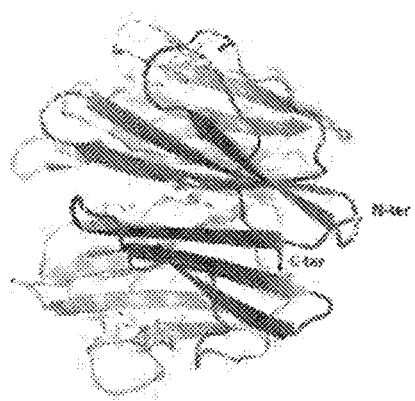
5B
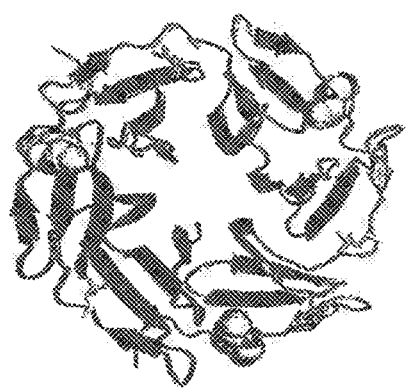
5C

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Linker

<400> SEQUENCE: 1

Ser Ser Thr Val Pro Gly Asp
1               5

<210> SEQ ID NO 2
<211> LENGTH: 90
<212> TYPE: PRT
<213> ORGANISM: Ralstonia solanacearum

<400> SEQUENCE: 2

Ser Ser Val Gln Thr Ala Ala Thr Ser Trp Gly Thr Val Pro Ser Ile
1               5                   10                  15

Arg Val Tyr Thr Ala Asn Asn Gly Lys Ile Thr Glu Arg Cys Trp Asp
                20                  25                  30

Gly Lys Gly Trp Tyr Thr Gly Ala Phe Asn Glu Pro Gly Asp Asn Val
            35                  40                  45

Ser Val Thr Ser Trp Leu Val Gly Ser Ala Ile His Ile Arg Val Tyr
        50                  55                  60

Ala Ser Ser Gly Thr Thr Thr Glu Trp Cys Trp Asp Gly Asn Gly
65                  70                  75                  80
```

-continued

```
Trp Thr Lys Gly Ala Tyr Thr Ser Thr Asn
                85                  90
```

LECTINS AND APPLICATIONS FOR THE DETECTION OF PATHOLOGICAL STATE MARKERS

One object of the invention is to provide novel lectins, usable, in particular, for specifically detecting labels of pathological conditions.

Lectins are proteins, of eukaryotic or prokaryotic origin, which are linked to mono-, oligo- and polysaccharide sugars, generally reversibly, with a strong specificity, without modifying them. On the cell surface, the sugars are present in glycoconjugates resulting from the linking thereof to proteins or lipids. The term "glycan" is generally utilised to designate the glycoconjugate sugars.

Lectins are usually multimeric proteins, through oligomerisation or tandem repetition of monomeric units (also designated by the term "modules" hereinafter), which provides them with a key role in agglutination, cell surface affinity, glycolipid recruitment or even tissue labelling.

The peptide chains of each module have C-ter and N-ter ends and comprise glycan binding sites.

Many biological functions, for example cell signalling, cell migration, immune recognition, or even interaction with pathogens, involve interactions between proteins and glycans. Taking advantage of these interactions however comes up against difficulties encountered in determining the structure of sugars involved.

A significant effort has been made in recent years to investigate their functions and mechanisms of the association thereof with specific ligands.

The production of new lectins by bioengineering remains however challenging to date.

Taking advantage of their experience in this field, the inventors focused their research to the production of novel non-natural lectins, also called neolectins hereinafter, using the concept of natural multivalence of lectins and starting from lectins having a basic architecture suitable for the recognition of sugars at the outer surface of the cells. This approach permitted to create, from existing lectins, neolectins having modulable valence and/or specificity, having great interest in diagnostic applications, in particular in cancerology.

Therefore, the invention aims at novel lectins or neolectins, having a great purity with an optimised specificity.

It also aims at a method for obtaining these neolectins, based on the molecular engineering of lectins having a prokaryotic or eukaryotic origin, allowing highly specific products to be available in a great amount, reproducibly and to a lesser cost, in comparison with the production of antibodies directed against oligosaccharidic epitopes.

Another object of the invention is to provide new oligosaccharidic labels with a great specificity, for the recognition of cells, in particular of some pathological conditions, such as cancerization.

It also aims at the application thereof for the specific detection of glycoconjugates, being labels of other pathological conditions.

Neolectins can also be applied to identify glycans in other fields of application: characterisation of molecules or cells in a research laboratory, quality control in pharmaceutical or food productions.

Lectins making up the basic architecture for neolectins of the invention are also designated by "reference lectins" hereinafter. These are multimeric proteins with a β-propeller type architecture, formed by monomer modules of about 30 to 60 amino acids, in which the glycan binding sites are located on a same side of the proteins and the C-ter and N-ter ends of the peptide chains on the other side of the proteins, which provides them with very strong properties of binding to glycans of cell surfaces.

The invention aims at neolectins of this type, characterised in that they are formed by 4 to 7 monomer modules, a single, or several, or all of the adjacent modules being linked to each other by linkers linking the N-terminal end of a module to a C-terminal end of the adjacent module.

According to this embodiment, the invention aims at a monomeric neolectin, formed by a single peptide chain with respectively a free C-ter end and a free N-ter end, and including linkers linking the other C-ter and N-ter ends of the adjacent constituent modules of the lectin.

The linkers are identical or different, and comprise peptide sequences with a sufficient size to link the C-ter and N-ter ends and advantageously include from 2 to 10 amino acids.

It will be understood that this arrangement provides neolectins with different valences, ranging from monovalence to multivalence.

More particularly, the invention aims at neolectins as defined above, characterised in that they include, with respect to the reference lectins, peptide chains with zero, one, or several mutations in the glycan binding site of one or more monomeric modules.

These mutations in lectins result in modulating the specificity by knocking out, as desired, zero, 1 or several glycan binding sites.

The monomeric neolectin of this embodiment is multivalent, having several glycan binding sites, or monovalent having a single glycan binding site.

According to an advantageous arrangement of this embodiment, the monomeric, multivalent or monovalent neolectin is a recombinant protein including linkers between modules and that can also comprise one or more mutations in one or several glycan binding sites of at least 1 constituent module, with respect to the reference lectin. This arrangement provides the neolectin with a given specificity, which can be modulated or modified as described hereinafter in relation with the method for obtaining it.

These recombinant neolectins have the advantage of great purity and reproducibility.

The basic architecture of these neolectins advantageously corresponds to that of eukaryotic or prokaryotic lectins the crystallographic structures of which are known.

These are multimeric lectins having a spatial proximity of the N-terminal and C-terminal ends of adjacent monomers, suitable for being transformed into neolectins in accordance with the invention.

For example, it can mentioned RSL (*Ralstonia solanacearum* lectin), BambBL (*Burkholderia ambifaria* lectin), BC2LC-nt (*Burkholderia cenocepacia* lectin), HPA (*Helix pomatia* lectin), discoidin (*Dictyostelium discoideum* lectin), CTX-B (cholera toxin lectin) lectins and other B5 type bacterial toxins, AAA (*Anguilla anguilla* lectin) and adenovirus lectin.

The crystallographic structures of RSL and HPA, resolved by the inventors, are given in FIG. 1.

According to an arrangement of the invention, taken in combination with any of the definitions above, the neolectin comprises, on the side including the C-ter and N-ter ends of the peptide chains, one or more lysine type functional groups including an amine group which can be coupled with molecules enabling the labelling such as fluorophores and biotin and which can be activated to attach the lectin on a surface for example an Elisa plate, a gold chip, or a glass chip.

The invention also aims at a method for obtaining the neolectins defined above.

This method is characterised in that it comprises, adding, in a reference lectin such as defined above, linker sequences linking the C-ter and N-ter ends of the adjacent monomer units, to at least two adjacent modules keeping their respective free C-ter and N-ter ends.

A multivalent monomeric neolectin, consisting of a single peptide chain is obtained when all the C-ter and N-ter ends have been linked to each other except for a site formed by 2 adjacent units with their free C-ter and N-ter ends, respectively.

The linkers are introduced by protein engineering by inserting a sequence of nucleic acids between the sequences coding for the peptide chains of the constituent modules of the reference lectin.

The step of passing from a multivalent multimeric lectin to a monovalent monomeric lectin is advantageously coupled to a step of knocking out at least one site of binding the peptide chains to glycans, which enables the lectin affinity to be modified.

In a preferred embodiment of the invention, the knocking out step is made by point mutagenesis in the peptide chain by modifying the nucleic sequence coding for one or more of the amino acids involved in binding to the sugar as identified by crystallographic analysis and by replacing it with the sequence coding the desired amino acids.

The structural data acquired for the targeted lectins provide a fine knowledge of their oligosaccharide binding sites. The amino acids involved in the binding to the sugars (hydrogen bonding, hydrophobic contact, electrostatic interaction) can be very accurately targeted. By site directed mutagenesis, it is consequently easy to replace the important acid(s) for sugar binding with another which will not interact.

By virtue of the engineering of the gene with a controlled degeneracy, it is possible to selectively knock out the site(s) of binding to the protein chain to achieve the chosen valence.

By knocking out all the glycan binding sites, except for a single one, a monovalent and monomeric neolectin which can be handled by conventional protein engineering tools is obtained. From the knowledge of the protein crystallographic structure, a specificity to a glycan of biological interest can consequently be obtained.

If desired, the multivalence of the lectin can be partly or fully restored.

In another embodiment of the invention, the directed evolution is made by phage displaying the lectin library with a great diversity of amino acids in the loops forming the recognition sites. Therefore, it is possible to select the interesting mutants, for example on magnetic beads carrying the target epitope, and then to characterise their specificity.

Different techniques (ELISA, sugar chip . . . ) enable the specificity of neolectins to be checked. Their affinity for target oligosaccharide epitopes can be measured for example by binding microcalorimetry and surface plasmon resonance.

Monovalent neolectins the specificity of which has been modified can be used as such, after labelling with fluorescent molecules on the loops accessible on the face remote from the glycan site. They can also be transformed into multivalent lectins by mutagenesis by modifying each of the previously knocked out sites to assign them the new specificity. These multivalent neolectins have a very strong affinity to glycoconjugates present at the surface of the cell membranes. The labelling thereof on the face opposite to binding sites enables them to be used thereafter for the optimum recognition of the cell surface glycosylation.

Depending on the valence and specificity, these neolectins can be used, as a product or drug, in several fields of application involving the recognition of glycosylation epitopes at the cell surface, as cell and tissue labelling, targeting and vectorization, or viral infection inhibition of for example HIV.

They can also be used for the recognition of glycosylation of natural or recombinant proteins with a field of application in research laboratories or in quality control in the production of recombinant proteins such as therapeutic antibodies.

These fields of application range from research in glycobiology (glycome analysis by lectin chips, glycoconjugate purification columns, labelling of modified cells . . . ), to medical diagnostics (glycosylation change identification associated with some pathological conditions such as inflammation and cancer), biotechnology (glycosylation control of recombinant proteins produced into eukaryotic cells, such as therapeutic antibodies) to therapeutic applications (targeting active compounds and cell internalization, inactivation of virus entry points for some viruses).

The application of neolectins for diagnostics and follow-up of some cancer tumours turns out to be of a great interest for detecting tumours and their windows, as well as the follow-up of their improvement or degradation in the case of a treatment.

These neolectins can also be used on chips in order to refine and standardise diagnostics.

It should be noted that the neolectins of the invention can be compared to antibodies directed to glucidic epitopes, but have the advantage of being possibly produced in an easier way, in great amounts and thus at a lesser cost.

The neolectins will be produced into bacteria or eukaryotic cells by the conventional biotechnology techniques. Tags or further protein domains could be fused with the neolectins to assist in producing or purifying them. These fields could be cleaved from the neolectins or not, depending on the applications contemplated.

Further characteristics and advantages of the invention will be given in the following examples and are illustrated in FIGS. 1 to 5, which represent respectively, FIG. 1, multimeric lectins used according to the invention, having their binding sites on the same side of the protein FIGS. 2A to 2D, the scheme of production of neolectins with valence and specificity being modulable by protein engineering, FIG. 3, bottom and side views with linkers of a RSL and HPA neolectin, FIGS. 4A to 4C, the inactivation of a recognition site in peptide chains of 3 RSL modules FIGS. 5A to 5C, two orthogonal views (5A and 5B) and a bottom view of the crystallographic structure of a RSL neolectin complexed with fucose (5C).

EXAMPLE 1

Scheme of Production of a Monovalent Monomeric Neolectin by Transforming a Reference Lectin As illustrated in FIGS. 2A to 2D, a multimeric multivalent reference lectin (2A) formed by 6 repeat modules is used, each module being formed by a peptide chain including 2 terminal ends, respectively N-ter and C-ter and including a glycan binding site represented by "0".

Linkers are added to link the C-ter and N-ter ends of 2 neighbouring modules, except for 2 adjacent C-ter and N-ter ends left free, which results in a multivalent monomeric lectin (2B), formed by a single peptide chain.

By point mutagenesis based on the structural knowledge of the lectin, a monovalent monomeric lectin (2C) is obtained. The specificity of the lectin (2C) is modified as desired (directed evolution by phage display or point mutations based on the structural knowledge) to obtain neolectins having controlled valence and specificity (2D).

EXAMPLE 2

Obtaining RSL Neolectins with a Controlled Valence

A RSL neolectin formed by 3 dimer units 1-2, 3-4 and 5-6 is used.

The units 2;3 and 4;5 are linked by a linker with a sequence SEQ ID NO:1: SSTVPGD selected because of its similarity with natural linkers. The nucleotide sequence coding for this peptide is inserted between the sequences coding for the peptide units to link between them the C-ter and N-ter ends in 2;3 and 4;5. The nucleotide sequences coding for the units 1-2, 2-3 and 4-5 have been modified beforehand to have differences between them.

This strategy enables the binding sites to be modified, and thus the valences to be modified at the chosen positions, which results in different topologies.

FIG. 3 represents a RSL neolectin consisting of 3 modules of the RSL reference lectin, whose sequence is represented as SEQ ID NO:2, which are linked by the linkers in a bottom view and in a side view. A representation is also given for a HPA lectin with linkers.

By site directed mutagenesis, an Arginine in position 17 of the initial peptide chain of 3 RSL modules has been replaced by an Alanine in order to remove the contact with the glycan.

Figure 4A:
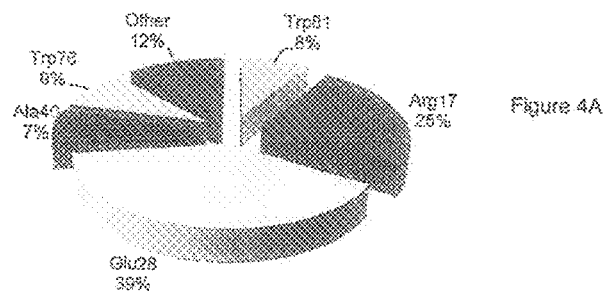
Figure 4B:
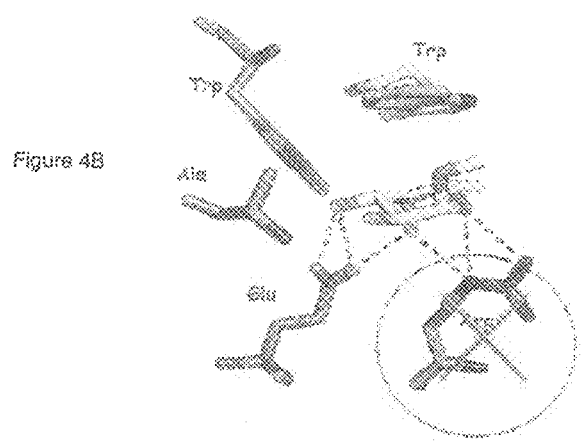
Figure 4C:
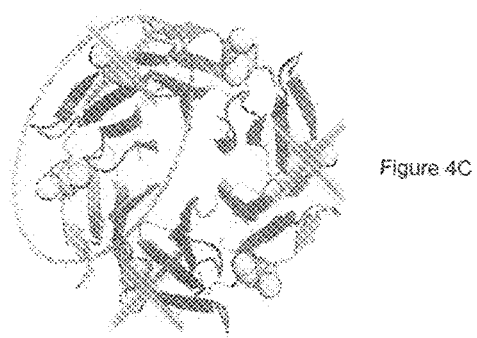

FIGS. 4A, 4B and 4C, with reference to SEQ ID NO: 2, show the sugar recognition site (4A: the respective contributions of amino acids of the binding site to the sugar in terms of binding energy), the knock out of the Arg site in position 17 (4B) of the initial peptide chain of the RSL module and the lectin with its 3 knocked out Arg sites (4C).

EXAMPLE 3

Crystallographic Structure of a Neolectin Obtained by Protein Engineering

The protein has been built from the triple replication of a RSL gene with the inclusion of binding sequences as described above. The protein has been produced recombinantly in *E. coli* and has been characterised. The affinity to fucose is identical to that of the reference lectin, and the stoichiometry is indeed of 6 fucose sites per protein.

FIGS. 5A and 5B show that the neolectin does fold as a β-propeller type architecture, with six intact fucose sites, as the reference lectin. The two peptide bonds which have been inserted have some flexibility: the first one is visible in the electronic density map whereas the other is more flexible.

The crystallographic structure of the neolectin/fucose complex is given in FIG. 5C with a resolution of 1.35 Ang.

From this monovalent monomeric neolectin, it is possible to reintroduce one or more binding sites.

The invention claimed is:

1. A monomeric, single polypeptide chain lectin having a β-propeller architecture, said lectin comprising 4 to 7 peptide modules, wherein each module comprises about 30 to 60 amino acids;

wherein each module comprises a glycan binding site;

wherein at least one glycan binding site comprises at least one mutation, said mutation altering glycan binding;

wherein each module is linked to another module with a peptide linker; and wherein at least one peptide linker is an exogenous peptide linker.

2. The lectin of claim 1, wherein the peptide linkers are the same or different, wherein the peptide linkers comprises 2 to 10 amino acids.

3. The lectin of claim 1, wherein the lectin is multivalent and capable of binding more than one glycan or the lectin is monovalent and binds a single glycan.

4. The lectin of claim 1, wherein the lectins comprises one or more lysine functional groups, wherein the lysine functional groups comprise a label.

5. The lectin of claim 4, wherein said label is a fluorophore or biotin.

6. The lectin of claim 1, wherein the peptide modules are derived from RSL (*Ralstonia solanacearum* lectin), BambBL (*Burkholderia ambifaria* lectin), BC2LL-nt (*Burkholderia cenocepacia* lectin), HPA (*Helix pomatia* lectin), discoidin (*Dictyostelium discoideum* lectin), CTX-B (cholera toxin lectin) lectins, B5 type bacterial toxins, AAA (*Anguilla anguilla* lectin), and adenovirus lectin.

7. A method for producing the monomeric, single polypeptide chain lectin of claim 1, said method comprising:

transforming a host cell with nucleic acid encoding the monomeric, single chain lectin, culturing said host cell in culture medium under conditions for the expression of the monomeric, single polypeptide chain lectin, isolating the monomeric, single polypeptide chain lectin from the host cells or the culture medium.

8. A method for identifying glycosylation epitopes on a cell surface in vitro, said method comprising:

contacting cells with the lectin of claim 1, wherein the glycosylation epitopes are identified when the lectin binds to the cell surface glycan.

* * * * *